US011849782B2

(12) United States Patent
Cohen et al.

(10) Patent No.: US 11,849,782 B2
(45) Date of Patent: Dec. 26, 2023

(54) FACEMASK

(71) Applicants: Scott A Cohen, Portland, ME (US); Michael B. Tyberghein, Roswell, GA (US)

(72) Inventors: Scott A Cohen, Portland, ME (US); Michael B. Tyberghein, Roswell, GA (US)

(73) Assignee: AMERICAN BIOMEDICAL GROUP INC., Oklahoma City, OK (US)

( * ) Notice: Subject to any disclaimer, the term of this patent is extended or adjusted under 35 U.S.C. 154(b) by 638 days.

(21) Appl. No.: 17/018,711

(22) Filed: Sep. 11, 2020

(65) Prior Publication Data

US 2022/0079263 A1 Mar. 17, 2022

(51) Int. Cl.
*A41D 13/11* (2006.01)
*A61L 9/16* (2006.01)
*A62B 19/00* (2006.01)
*A62B 18/02* (2006.01)
*A62B 23/02* (2006.01)
*A61L 101/30* (2006.01)

(52) U.S. Cl.
CPC ...... *A41D 13/1138* (2013.01); *A41D 13/1161* (2013.01); *A61L 9/16* (2013.01); *A62B 18/025* (2013.01); *A62B 19/00* (2013.01); *A62B 23/02* (2013.01); *A61L 2101/30* (2020.08)

(58) Field of Classification Search
CPC .......... A41D 13/1138; A41D 13/11; A41D 13/1107; A41D 13/1115; A41D 13/1123; A41D 13/113; A41D 13/1146; A41D 13/1192; A41D 13/1161; A61L 9/16; A61L 9/22; A61L 2/022; A61L 2/03; A61L 2/035; A61L 2/18; A62B 18/025; A62B 18/02; A62B 19/00; A62B 19/02; A62B 23/00; A62B 23/02
See application file for complete search history.

(56) References Cited

U.S. PATENT DOCUMENTS

| 6,522,918 | B1 | 2/2003 | Crisp et al. |
| 7,457,667 | B2 | 11/2008 | Skiba |
| 7,813,806 | B2 | 10/2010 | Skiba |
| 8,091,551 | B2 | 1/2012 | Messier |
| 8,744,567 | B2 | 6/2014 | Fassih et al. |
| 2010/0272668 | A1* | 10/2010 | Matsushita ............... D01F 6/52 526/318.2 |

(Continued)

FOREIGN PATENT DOCUMENTS

KR 20110026744 A * 3/2011 ........... A62B 18/025

OTHER PUBLICATIONS

English Machine Translation of KR-20110026744-A provided by PE2E (Year: 2011).*

*Primary Examiner* — Joseph D. Boecker
*Assistant Examiner* — Brian T Khong
(74) *Attorney, Agent, or Firm* — Terry M. Sanks, Esq.; Beusse Sanks, PLLC

(57) ABSTRACT

A respiratory face mask having a breathing cartridge therein which face mask breathing cartridge can both filter the breathing air while passing the breathing air through a voltage being generated by the cartridge. The cartridge generates a galvanic cell using spaced apart dissimilar metal particles when immersed in an electrolyte being held by an adjacent hydration layer of liquid retaining foamed polymer having breathing passageways therethrough.

18 Claims, 5 Drawing Sheets

(56) References Cited

U.S. PATENT DOCUMENTS

2011/0094514 A1* 4/2011 Rakow .................. A62B 19/00
128/205.27
2020/0114178 A1* 4/2020 Waterford .............. A62B 23/02

* cited by examiner

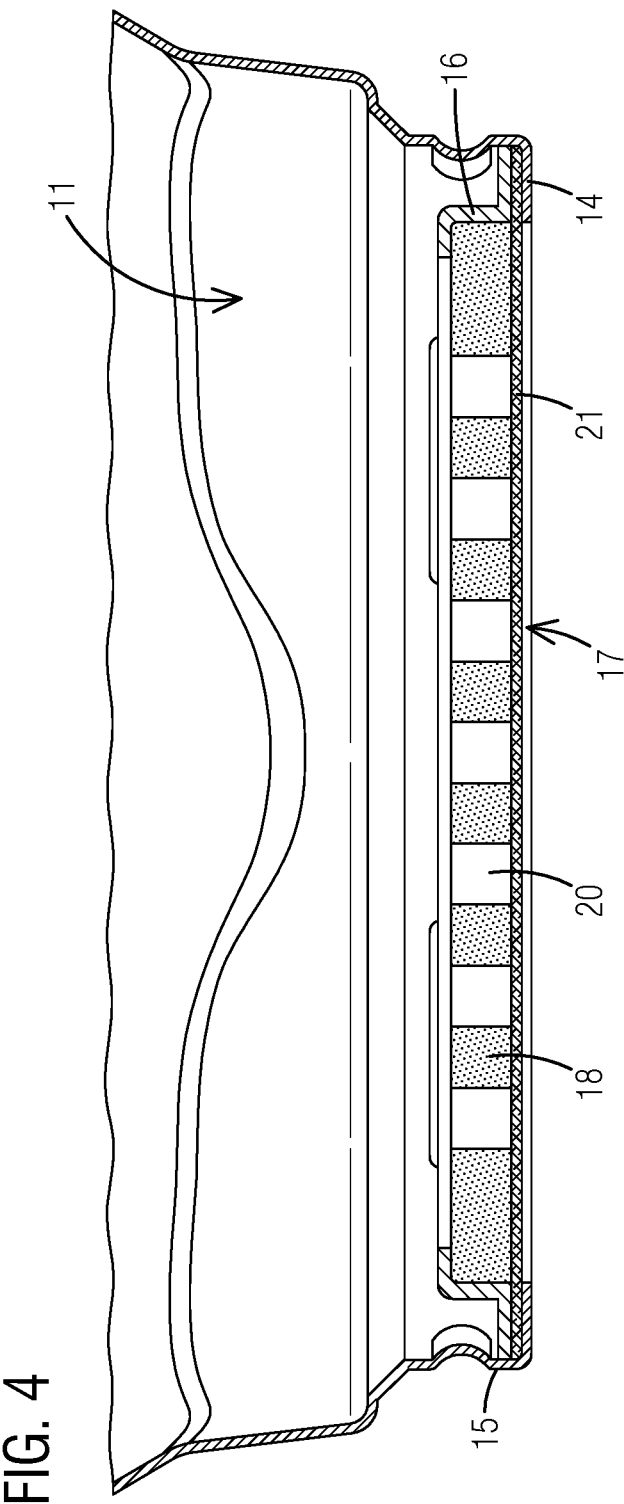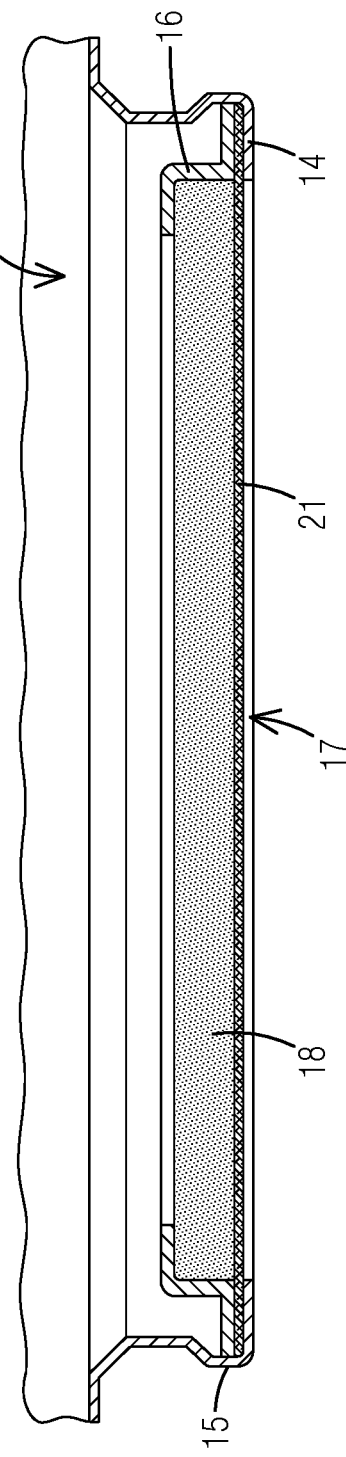

FACEMASK

FIELD OF THE INVENTION

This invention relates to a respiratory face mask having a breathing cartridge therein and especially to face mask breathing cartridge which can both filter the breathing air while passing the breathing air past a voltage being generated in the cartridge.

BACKGROUND OF THE INVENTION

Face masks find utility in a variety of medical, industrial and household applications by protecting the wearer from the inhaling dust and other harmful airborne contaminates through their mouth or nose. The use of face masks is a recommended practice in the healthcare industry to help prevent the spread of disease. Face masks worn by healthcare providers help reduce infections in patients by filtering the air exhaled from the wearer, thus reducing the number of harmful organisms or other contaminants released into the environment. Additionally, face masks protect the healthcare worker by filtering airborne contaminants and microorganisms from the inhaled air.

The recent outbreak of severe acute respiratory diseases has elevated interest in germicidal masks which can deactivate microbes contacting the face mask so that they are not inhaled by the wearer and so that they are not transferred to another surface by inadvertent contact of the mask on other surfaces or the hands.

The most commonly used particulate filtering face piece respirator has the N95 classification meaning that it filters at least 95% of air borne particles. It passes the ASTM test to filter 95% of the NaCL molecules for a period of time. This filter requires a fine mesh of synthetic polymer fibers such as non-woven polypropylene fabric. It is produced by melt blowing and forms the inner filtration layer that filters out hazardous particles.

Some metals immersed in an electrolyte, such as tap water or sea water, can produce an electric voltage. When two dissimilar metals are juxtaposed next to each other and placed in an electrolyte they produce a galvanic cell to produce a voltage. Silver and copper are well documented biocides that have been shown to kill bacteria, fungi and certain viruses. Both silver and copper can also be used as a cathode in a galvanic cell with a more active metal, such as zinc, used as an anode to produce an electric voltage. It has been shown that combining the use of small silver particles with a small electrical current can reduce bacteria growth better than just the silver.

Prior art U.S. Pat. Nos. 7,457,667 and 7,813,806 to Skiba teach the use of bandages that have a layer of dissimilar metals, such as silver and zinc, printed on the surface thereof for generating an electric current when in contact with an electrolyte. The electrolyte may be sodium chloride or the wound fluid that the bandage is covering. Other skin treatment deices include the Fassih et al. U.S. Pat. No. 8,744,567 for a galvanic skin treatment device and in U.S. Pat. No. 6,522,918 to Crisp et al. for an electrolytic device which uses a silver bearing material along with zinc to generate a low voltage for treating tissue. The Messier U.S. Pat. No. 8,091,551 is for a facemask with a filtering closure having a porous gasket around the periphery of the facemask for abutting the face. The gasket creates a breathable enclosure and may incorporate a porous dielectric carrier for producing an electrostatic charge.

The present invention is for a face mask that incorporates a filter cartridge to reduce or kill bacterial agents in the air passing through the cartridge. The cartridge uses a cotton cloth having having small bits of a metal, such as silver particles, on the surface thereof, adjacent small bits of a dissimilar metal, such as zinc particles, which when immersed in an electrolyte solution forms a galvanic cell generating an electric voltage. A hydration sponge having breathing holes therethrough is mounted adjacent the cloth and when immersed or soaked in an electrolyte can keep the adjacent cloth immersed in electrolyte for a prolonged period.

SUMMARY OF THE INVENTION

This invention relates to a respiratory face mask formed with a polymer face shield shaped to cover a person's mouth and nose. The shield has a ring receptacle for holding a filter cartridge therein. The cartridge has a hydration sponge for holding an electrolyte solution therein which sponge may have a plurality of breathing openings therethrough for the passage of air and is shaped to fit into the ring receptacle. A commercially available cotton fabric having a plurality silver and zinc particles printed thereon is shaped to fit into the ring receptacle adjacent the hydration sponge. The silver particles and the zinc particles are spaced apart from each other on the cotton fabric for producing an electric voltage when the metal particles are immersed in an electrolyte such as tap water or a saline solution. A retainer ring holds the cartridge hydration member and cotton fabric in the face shield ring receptacle. Thus a respiratory face mask is capable of generating a voltage in a face mask when breathing through the cartridge to reduce or kill bacterial and viral agents.

BRIEF DESCRIPTION OF THE DRAWINGS

The accompanying drawings, which are included to provide further understanding of the invention, are incorporated in and constitute a part of the specification and illustrate an embodiment of the invention and together with the description serve to explain the principles of the invention.

In the drawings:

FIG. 4 is a side sectional view taken through the cartridge of the facemask of FIGS. 1-3;

FIG. 5 is a second side sectional view taken through the cartridge of the facemask of FIGS. 1-3.

DETAILED DESCRIPTION OF AN EXEMPLARY EMBODIMENT

Figure 1:
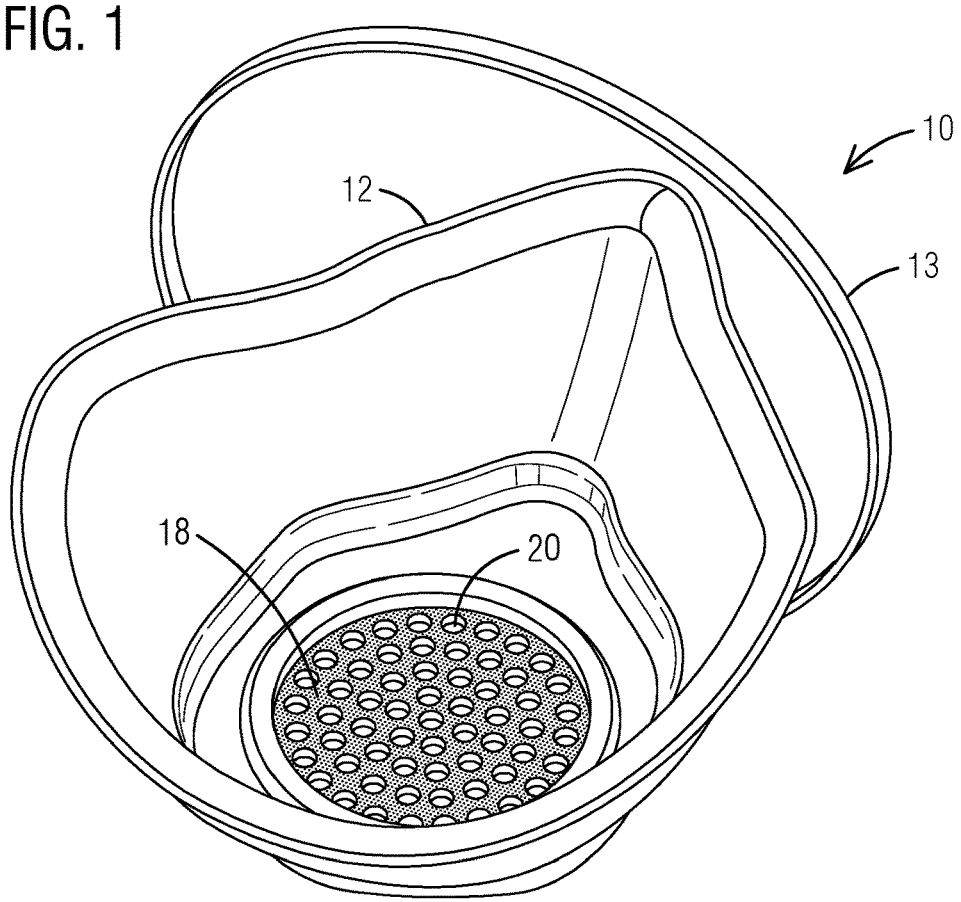
FIG. 1 is a rear perspective view of a facemask showing the hydration layer of the cartridge in accordance with the present invention.
Figure 2:
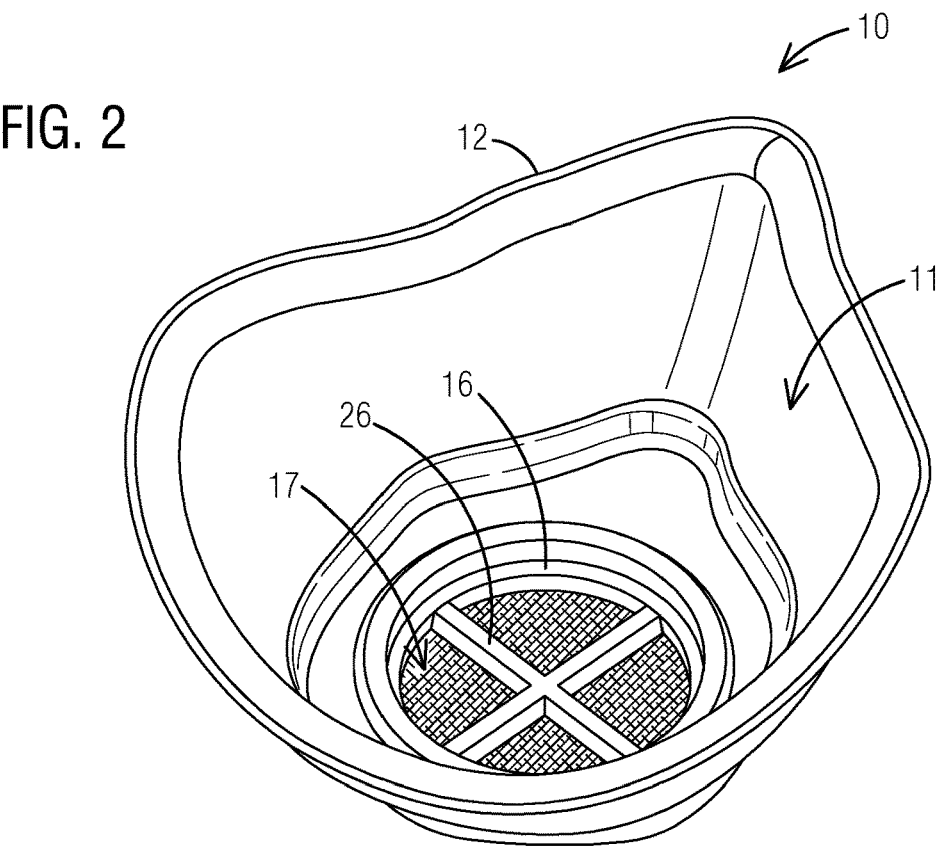
FIG. 2 is a rear perspective view of a the face mask of FIG. 1 having the fabric layer of the cartridge having dissimilar metal particles coated thereon.
Figure 3:
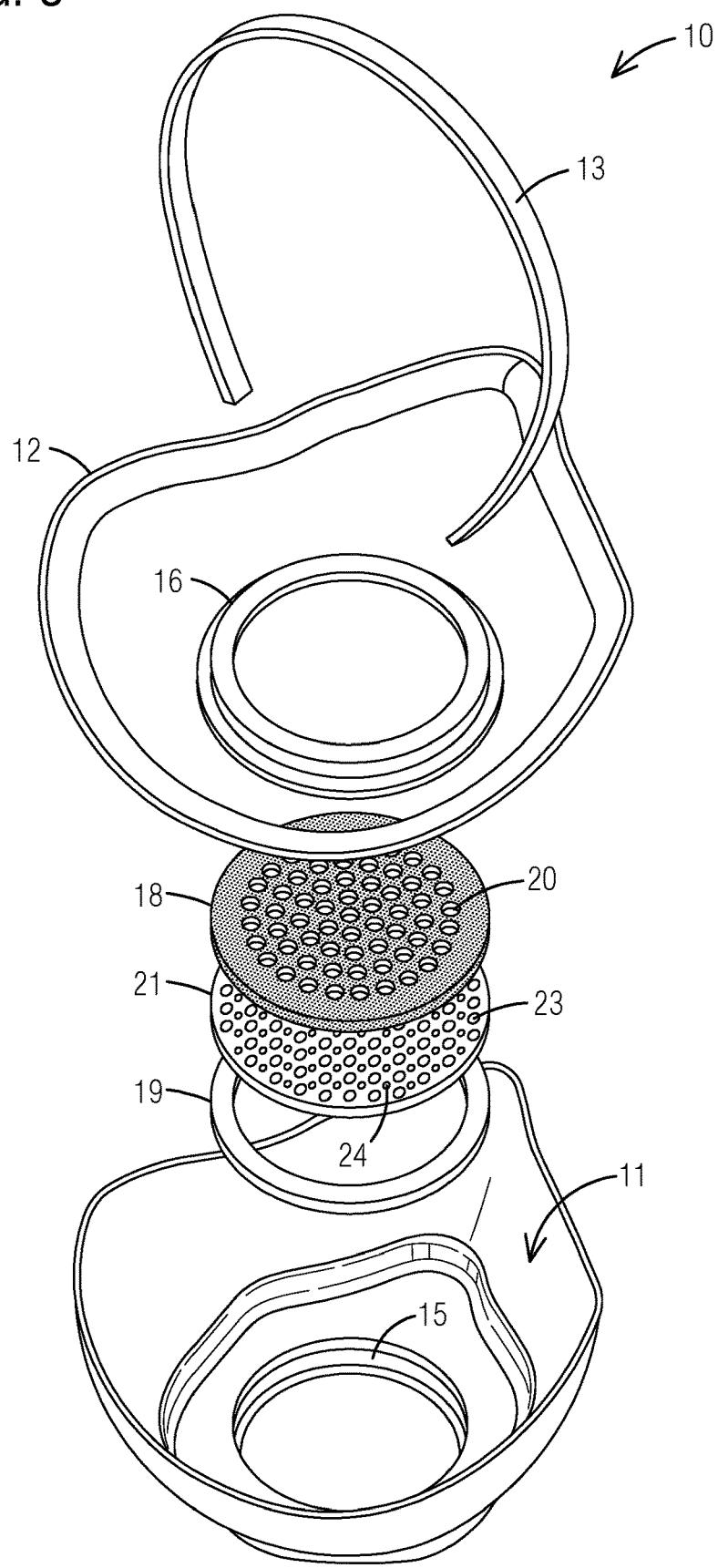
FIG. 3 is an exploded perspective view of the facemask of FIGS. 1 and 2.
Figure 6:
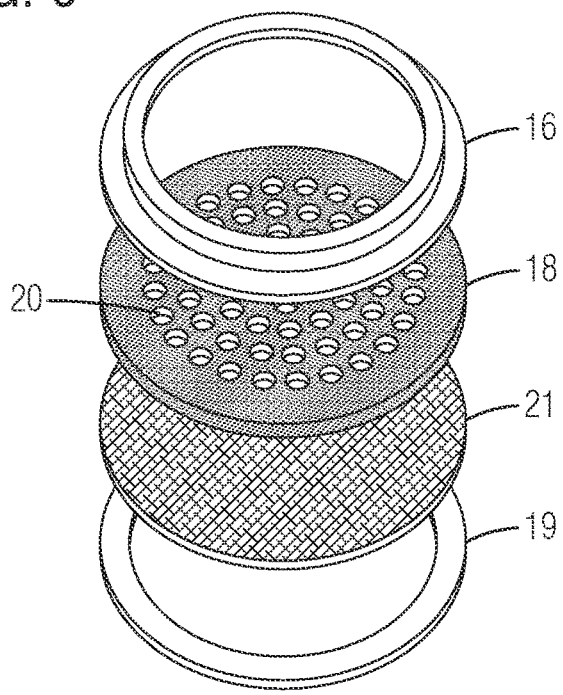
FIG. 6 is an exploded perspective view of the filter cartridge of the facemask of FIGS. 1 through 5.

Referring to the drawings FIGS. 1 through 6 and especially to FIG. 1 through 3, a facemask 10 has a face shield or facemask body 11 having a seal 12. The face mask can be made of a polymer such as a polypropylene or co-polymer polypropylene. The seal 12 seals the mask to a person face and may be made of rubber or of a polymer. The mask has a head band 13 for wrapping around the head or ears of a person wearing the mask. The mask has a cylinder shaped ring receptacle 15 for breathing through and for holding a filter cartridge therein. The ring receptacle 15 has a receptacle flange 14 on the front thereof for holding the cartridge therein. A retainer ring 16 holds the cartridge in the breathing opening from the rear of the ring receptacle.

Referring more specifically to FIGS. 3 through 6, the cartridge 17 can be seen as consisting of a hydration layer 18 which may be a foamed polymer, such as a liquid retaining polyurethane foam, having a plurality of apertures 20 therein to allow the passage of air therethrough. The cartridge 17 has a fabric layer 21, such as cotton, is first shaped and then positioned against the receptacle ring 15 flange 14 and may be held by an adhesive or by double sided tape 19 if desired. The cartridge 17 is held in place in the ring receptacle 15 by the retainer ring 16. The fabric 21, which is commercially available with silver 23 and zinc 24 particles printed on the surface thereof, has each silver particle 23 being spaced from a zinc particle 24 to create a galvanic cell when immersed in an electrolyte, such as tap or salt water to generate a voltage. It should be noted other dissimilar particles can also be used and can be attached to the fabric in other ways or attached to an N95 filter material which also filters the air of micro-particles passing therethrough. The metal particles can be incorporated in the fabric as long as the dissimilar metals are spaced from each other. The silver 23 forms the cathode while the zinc 24 forms the anode to form the galvanic cell. Other dissimilar metals, such as a copper cathode, may also be used. The hydration layer 18 foam can hold the electrolyte to allow for the production of a voltage for the air being breathed to pass through. The retainer ring 16 may have cross bars 26 to more firmly hold the cartridge members in place and may be held to the mask with a press or snap fit or the like. The mask may also include a layer of N95 filter material to remove fine particles as desired. Two layers of fabric 21 may also be used in the cartridge, placing one on either side of the hydration layer 18.

In operation, the mask cartridge 17 is immersed in an electrolyte, such as salt water, to saturate the hydration layer 18 and the fabric 21. The saturated hydration layer 18 then keeps the adjacent fabric 21 having the dissimilar metals 23 and 24 thereon wet with the electrolyte to form a galvanic cell and produce a voltage. Air breathed through the fabric and voltage field is generated to reduce or destroy microbes. The air passes on through the openings 20 of the hydration layer 18 as a person wearing the face mask breathes.

Figure 7:
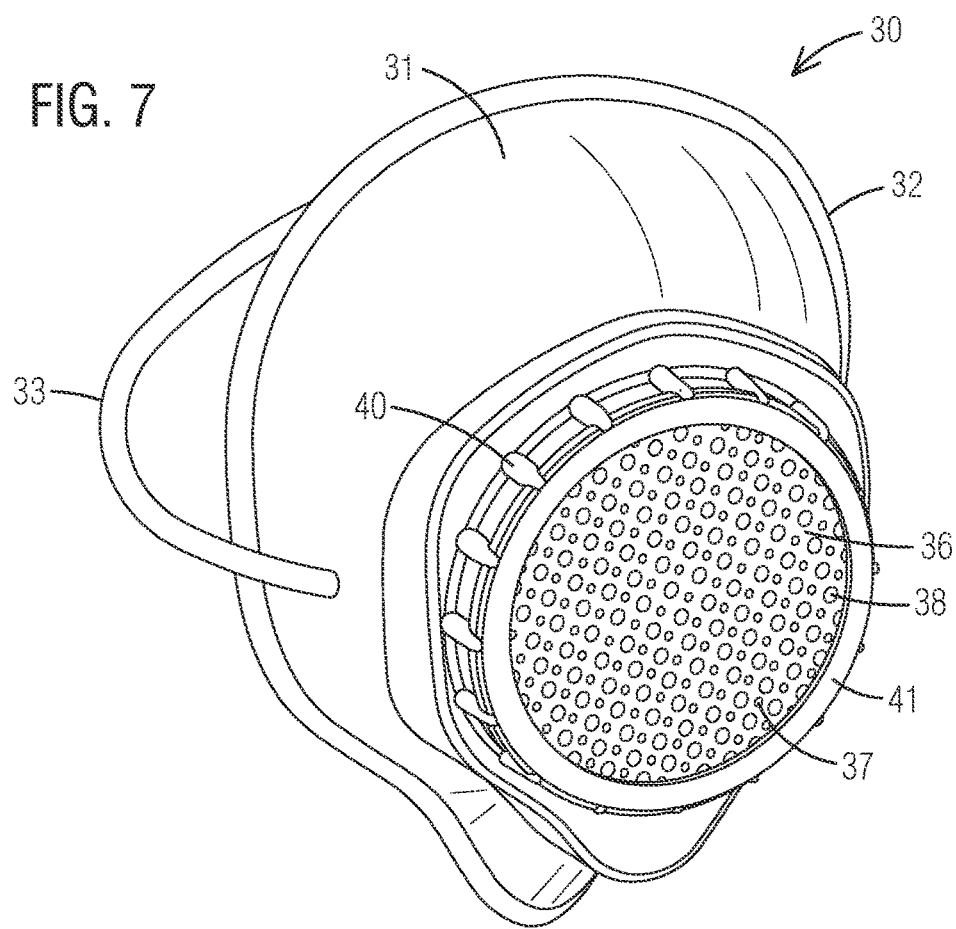
FIG. 7 is a front perspective view of a another embodiment of the of facemask of FIGS. 1 through 6 in accordance with the present invention.
Figure 8:
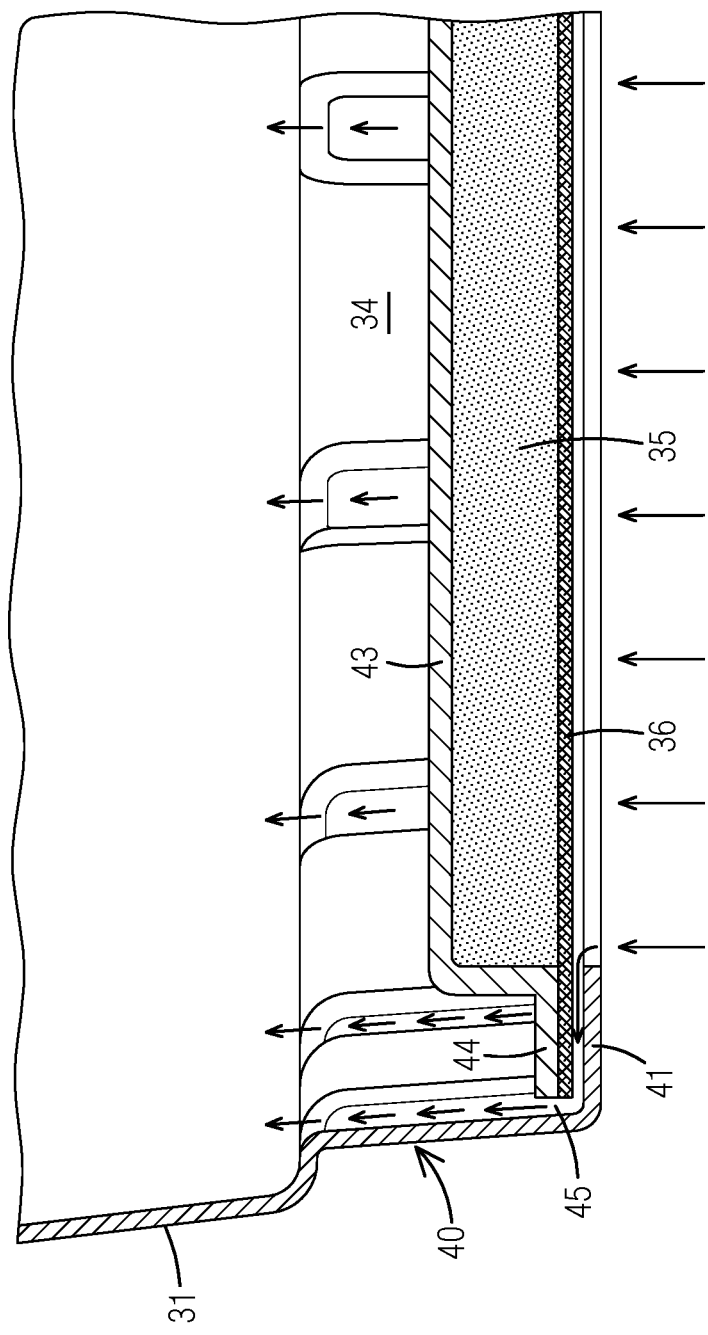
FIG. 8 is a side sectional view taken through the cartridge of the facemask of FIG. 7.

Referring to FIGS. 7 and 8 another embodiment of the present invention has a facemask 30 having a face shield 31 which may be made of a polymer, such as a polypropylene plastic and has a seal 32 to seal the face shield to a person face. The seal 32 may be made of rubber or of a polymer as desired. The mask 30 is held to a persons face with a headband 33. This mask extends the ring receptacle 40 out further from the basic shield 31 than in the embodiment of FIGS. 1 through 6. This allows for additional space 34 behind the cartridge components.

The cartridge components consists of a hydration layer 35 and a fabric layer 36 having a plurality of dissimilar metals printed thereon which cartridge components are the same as in the prior embodiment of FIGS. 1 through 6. The fabric layer may be made of cotton and has dissimilar metals placed or printed thereon, including the preferred silver 37 and zinc 38. The silver and zinc are spaced apart to create a voltage when immersed in an electrolyte. The hydration layer 35 can be saturated with an electrolyte such as salt water, to provide the electrolyte to the dissimilar metals on the fabric. The ring receptacle 40 has been extended outward and supported by posts 42 and has a flange 41 on the front thereof to hold the cartridge in the ring receptacle 40. The cartridge is held in place by the retainer ring 43. The retainer ring 43 has a flanged edge 44 that holds the fabric 36 loosely against the face shield flange 41. The retainer ring 43 flange 44 has been shortened to form a gap 45 to allow air to flow there around and can pass between the face shield flange 41 and retainer ring flange 44 over the fabric 36 and through the gap 45. This allows air to bypass going directly through the front of the cartridge while still passing through a voltage created by the dissimilar metals on fabric 36 to enter the space 34 when the breathing resistance increases from a fully saturated fabric 36. This passageway bypassing the direct passage of air through the breathing opening still has the air passing over through a voltage created by the dissimilar metals on the fabric 36. The passageway is illustrated arrows in FIG. 8.

It should be clear at this time that a facemask has been provided that will reduce or destroy microbes or the like. However the present invention is not to be considered limited to the forms shown which are to be considered illustrative rather than restrictive.

We claim:

1. A respiratory face mask comprising:
   a face shield for covering the mouth and nose, said face shield having a cartridge receptacle forming a breathing opening therethrough;
   a hydration member for holding an electrolyte solution therein, said hydration member having a plurality of openings therethrough for passage of air and shaped to fit into said cartridge receptacle;
   a fabric material having a plurality of dissimilar metal-particles thereon, said dissimilar metal particles being spaced apart on said fabric material for generating an electric voltage when immersed in the electrolyte solution, said fabric material being shaped to fit into said cartridge receptacle adjacent said hydration member and being held thereagainst; and
   a retainer member for holding said hydration member and said fabric material in said face mask cartridge receptacle;
   whereby the respiratory face mask can generate an electrical voltage field in said cartridge receptacle when said fabric material having said dissimilar metal particles thereon is immersed in the electrolyte solution.

2. The respiratory face mask in accordance with claim 1 in which said fabric material having said plurality of dissimilar metal particles thereon includes silver and zinc particles, each said metal particle being spaced from each other metal particle.

3. The respiratory face mask in accordance with claim 2 in which said hydration member is a polymer sponge capable of holding the electrolyte solution therein abutting said fabric material.

4. The respiratory face mask in accordance with claim 3 in which said polymer sponge is a polyurethane sponge.

5. The respiratory face mask in accordance with claim 3 in which said fabric material is made of cotton.

6. The respiratory face mask in accordance with claim 5 in which said face shield is made of a polymer.

7. The respiratory face mask in accordance with claim 6 in which fabric material has a surface and said silver and zinc particles screen printed on the surface.

8. The respiratory face mask in accordance with claim 6 in which the face shield has a periphery seal for sealing said face shield to a person's face.

9. The respiratory face mask in accordance with claim 3 in which said cartridge receptacle has a flanged end having said fabric material held thereto with an adhesive bonding agent.

10. The respiratory face mask in accordance with claim 1 in which the retainer member is a circular ring having crossed shaped bars.

11. The respiratory face mask in accordance with claim 10 in which said face shield has a headband for holding said face shield onto a person's head.

12. The respiratory face mask in accordance with claim 1 in which said cartridge receptacle protrudes from said face shield and has a flanged end thereon for holding said hydration member and said fabric material therein.

13. A respiratory face mask comprising:
a face shield for covering a person's mouth and nose, said face shield having a cartridge receptacle on a front thereof;
a hydration sponge for holding an electrolyte solution therein, said hydration sponge having a plurality of openings therethrough for a passage of air and shaped to fit into said cartridge receptacle;
a cotton fabric shaped to fit into said cartridge receptacle adjacent said hydration sponge, said cotton fabric having a plurality of zinc and silver particles thereon, said silver particles and said zinc particles being spaced apart from each other on said cotton fabric for producing an electric voltage when immersed in the electrolyte solution; and
a retainer member for holding said hydration sponge and said cotton fabric in said cartridge receptacle;
whereby the hydration sponge and the cotton fabric form a filter cartridge that is a voltage generating breathing cartridge when said cotton fabric is soaked. in the electrolyte solution.

14. The respiratory face mask in accordance with claim 13 in which said hydration sponge is a foamed polymer sponge capable of holding the electrolyte solution therein, abutting said cotton fabric.

15. The respiratory face mask in accordance with claim 14 in which said polymer sponge is a polypropylene sponge.

16. A respiratory face mask comprising:
a face shield for covering a mouth and nose, said face shield having a cartridge receptacle extending from a front thereof forming a breathing opening therethrough, said cartridge receptacle having an inward flanged end;
a filter cartridge shaped to fit intointer said cartridge receptacle, said filter cartridge comprising fabric material having a plurality of dissimilar metal particles thereon, said dissimilar metal particles being spaced apart on said fabric material for generating an electric voltage when immersed in an electrolyte solution, and a hydration member for holding the electrolyte solution therein;
a retainer member for holding said filter cartridge in said cartridge receptacle, said retainer member having an outward flanged end fitting over said hydration member with said inward flanged end adjacent said outward flanged end forming a passageway therebetween around said filter cartridge with a portion of said fabric material therein;
whereby the respiratory face mask is configured to bleed air around said filter cartridge.

17. The respiratory face mask in accordance with claim 16 in which said hydration member has a plurality of openings therethrough for a passage of air.

18. The respiratory face mask in accordance with claim 16 in which a gap is formed between the outward flanged end and said inward flanged end forming the passageway therearound.

* * * * *